United States Patent [19]

Raible

[11] Patent Number: 4,623,518
[45] Date of Patent: Nov. 18, 1986

[54] BLOOD OXYGENATOR

[75] Inventor: Donald A. Raible, Santa Ana, Calif.

[73] Assignee: Baxter-Travenol Laboratories, Inc., Deerfield, Ill.

[21] Appl. No.: 765,174

[22] Filed: Aug. 12, 1985

Related U.S. Application Data

[60] Continuation of Ser. No. 559,395, Dec. 8, 1983, abandoned, which is a continuation of Ser. No. 430,520, Sep. 30, 1982, abandoned, which is a continuation of Ser. No. 257,577, Apr. 27, 1981, abandoned, which is a division of Ser. No. 689,971, May 26, 1976, Pat. No. 4,268,476, which is a continuation-in-part of Ser. No. 584,464, Jun. 6, 1975, abandoned.

[51] Int. Cl.$^4$ ............................................. A61M 1/14
[52] U.S. Cl. ............................... 422/46; 128/DIG. 3; 261/DIG. 28; 422/47
[58] Field of Search ................ 422/46, 47; 435/2; 261/DIG. 28; 128/DIG. 3

[56] References Cited

U.S. PATENT DOCUMENTS

| | | | |
|---|---|---|---|
| 2,833,279 | 5/1958 | Gallion | 422/47 |
| 2,934,067 | 4/1960 | Calvin | 422/46 |
| 3,175,555 | 3/1965 | Ling | 128/DIG. 3 |
| 3,204,631 | 9/1965 | Fields | 422/46 |
| 3,468,631 | 9/1969 | Raible et al. | 422/46 |
| 3,488,158 | 1/1970 | Bentley et al. | 422/47 |
| 3,578,411 | 5/1971 | Bentley et al. | 422/47 |
| 3,615,238 | 10/1971 | Bentley et al. | 422/47 X |
| 3,764,271 | 10/1973 | Brumfield | 422/46 |
| 3,769,162 | 10/1973 | Brumfield | 422/46 X |
| 3,770,384 | 11/1973 | Brumfield | 422/47 |
| 3,870,470 | 3/1975 | Yoshida | 422/46 |
| 3,892,534 | 7/1975 | Leonard | 422/47 |
| 3,898,045 | 8/1975 | Bowley | 422/46 |
| 3,927,152 | 12/1975 | Kyrias | 261/122 |
| 3,978,176 | 8/1976 | Voegeli | 261/DIG. 28 |
| 3,994,689 | 11/1976 | De Wall | 422/46 |
| 4,065,264 | 12/1977 | Lewin | 422/46 |
| 4,203,945 | 5/1980 | De Wall | 422/47 |
| 4,248,828 | 2/1981 | Bentley et al. | 422/47 |

FOREIGN PATENT DOCUMENTS

| | | | |
|---|---|---|---|
| 302125 | 6/1971 | U.S.S.R. | 422/47 |

Primary Examiner—Barry S. Richman
Assistant Examiner—Lynn M. Kummert
Attorney, Agent, or Firm—Donald L. Barbeau

[57] ABSTRACT

A blood oxygenating device having an oxygenating chamber and a heat exchanger chamber. The oxygenating chamber consists of a bubbler chamber and a mixing chamber. Oxygen is introduced into the bubbler chamber through a porous diffusion means situated near the inlet of the bubbler chamber. Bubbles pass from the bubbler chamber into a mixing chamber which is provided with a plurality of secondary flow-producing deflectors to promote secondary flow of blood bubbles passing therethrough. The secondary flow results in a highly efficient oxygen-carbon dioxide transfer. The blood bubbles are then passed through a heat exchange chamber and a defoaming means prior to exiting the oxygenating device.

8 Claims, 8 Drawing Figures

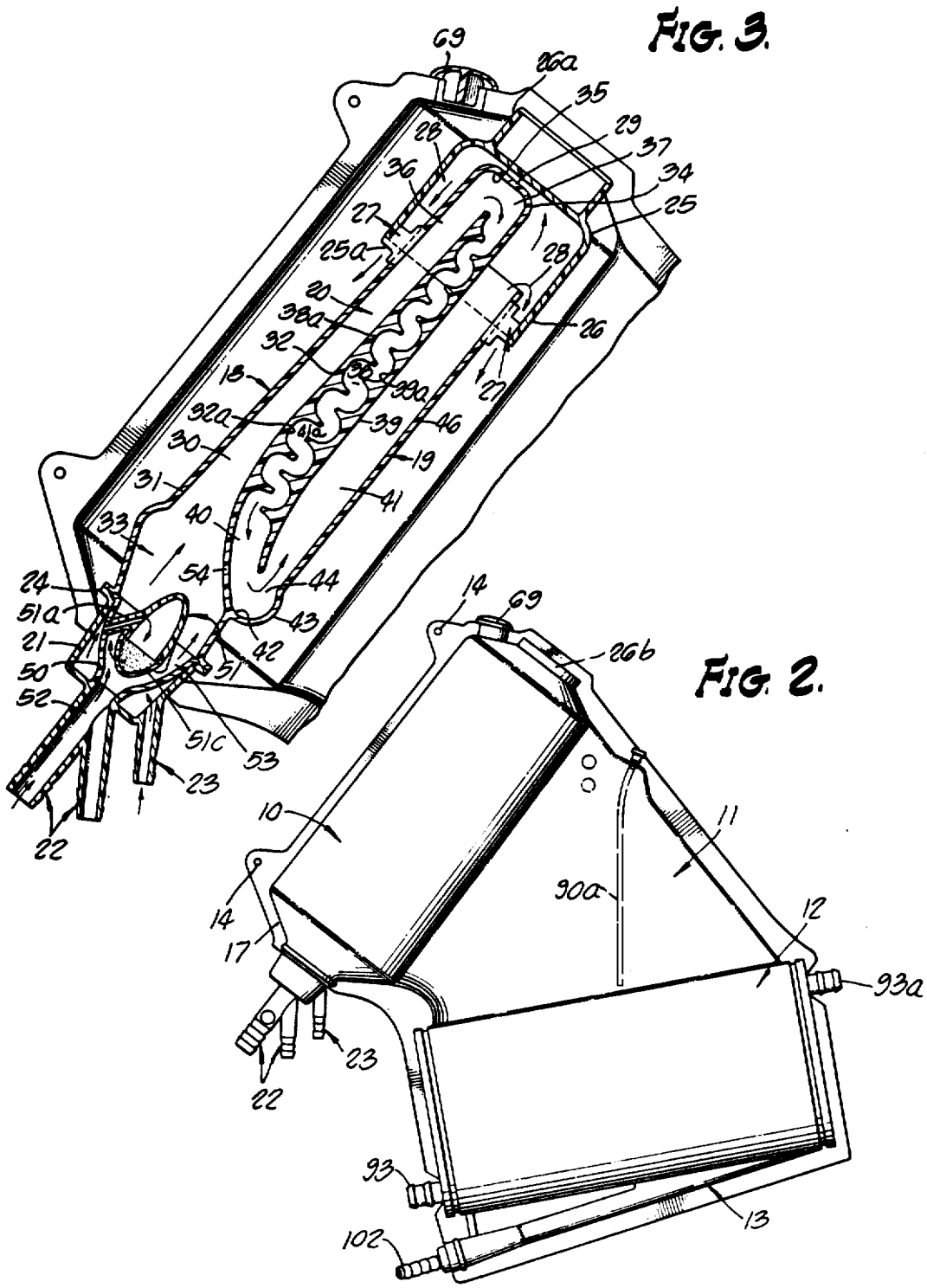

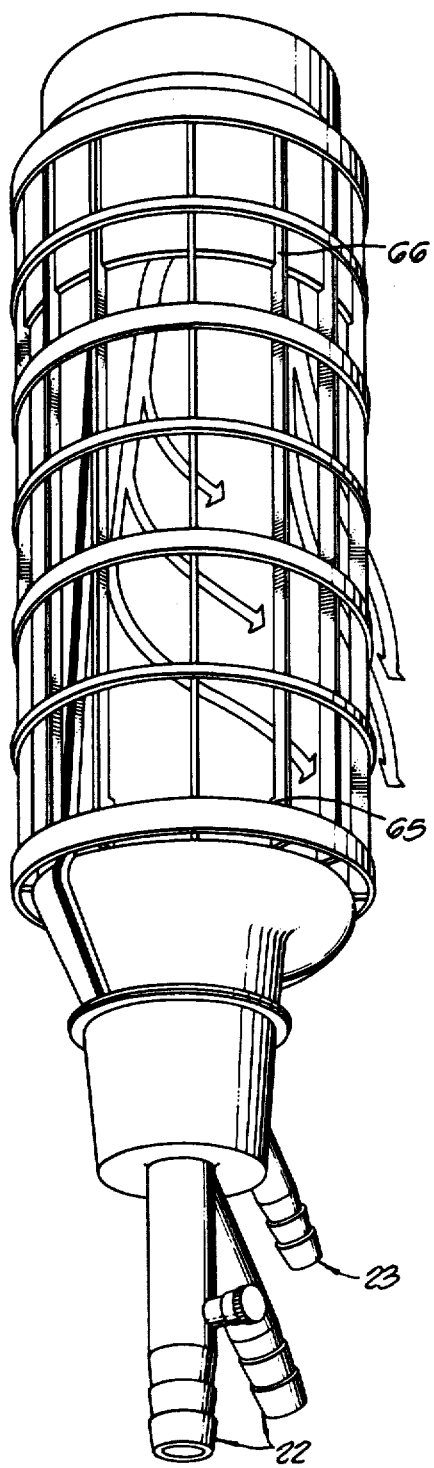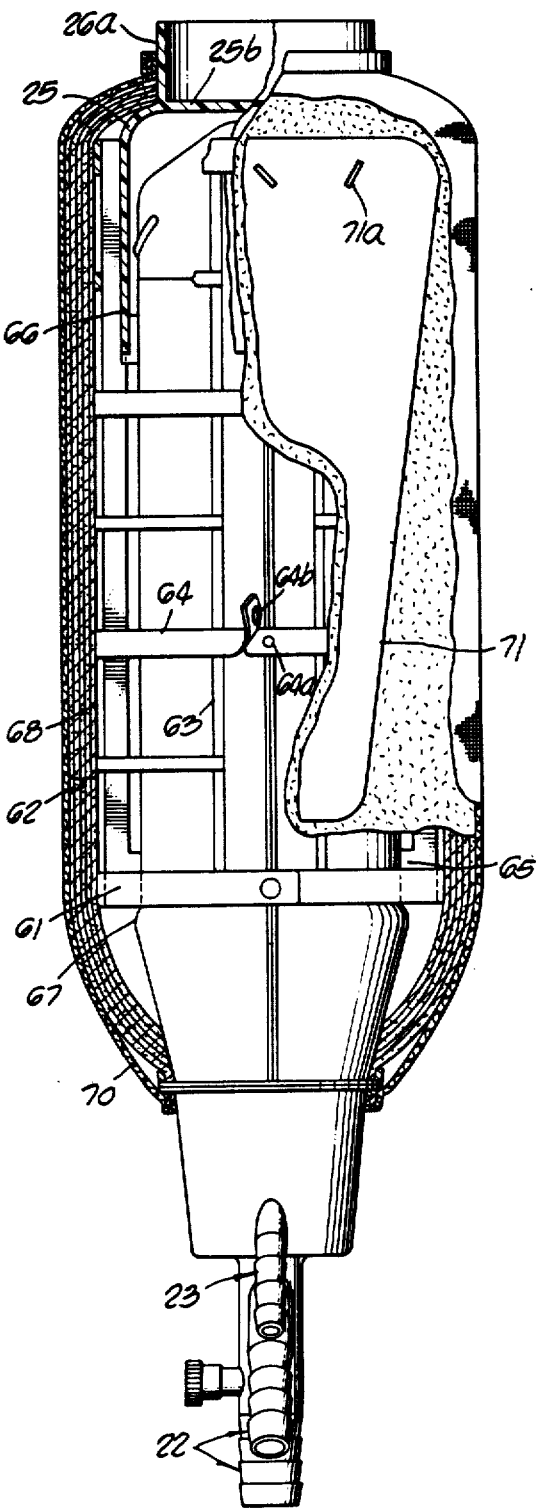

BLOOD OXYGENATOR

This application is a continuation of application Ser. No. 559,395, filed Dec. 8, 1983, now abandoned, which is a continuation of application Ser. No. 430,520, filed Sept. 30, 1982, now abandoned, which is a contination of application Ser. No. 257,577, filed Apr. 27, 1981, now abandoned, which is a divisional application of application Ser. No. 689,971, filed May 26, 1976, which is now U.S. Pat. No. 4,268,476, issued May 19, 1981, which in turn is a continuation-in-part application of application Ser. No. 584,464, filed June 6, 1975, now abandoned. The invertion herein relates to a bubble-type blood oxygenator of the kind used in thoracic surgery, and more particularly to an oxygenator having improved oxygen-carbon dioxide exchange.

BACKGROUND OF THE INVENTION

The present invention is a further improvement of the devices shown in the Bentley U.S. Pat. No. 3,615,238, issued Oct. 26, 1971, entitled "Oxygenator"; the Bentley, et al. U.S. Pat. No. 3,578,411 issued May 11, 1971, entitled "Bubbler Assembly for Blood Treating Apparatus"; the Bentley, et al. U.S. Pat. No. 3,488,158 issued Jan. 6, 1970, entitled "Bubbler Assembly for Oxygenator"; and application Ser. Nos. 436,913, now abandoned, and 565,043, now U.S. Pat No. 4,058,369, entitled "Blood Oxygenator" and "An Improved Oxygenating Device", respectively, the disclosures of which are incorporated by reference herein. These devices each represent important developments in the blood treatment art. However, since these devices temporarily assume the function of the heart and lungs of a patient during certain operations or other treatments of the body, further improvements are desired which will effect within such devices a blood treatment process as equivalent as possible to that natural process effected by the heart and lungs.

One aspect of the human oxygenating process which has heretofore been difficult to duplicate concerns the ratio of oxygen in the blood to carbon dioxide commonly expressed as the physiological ratio of $pO_2$ to $pCO_2$. In the past, oxygenating devices were either unable to maintain this $pO_2$ to $pCO_2$ ratio or, in an effort to maintain such a ratio over the range of flow rates required during operation of the devices, have operated inefficiently and/or in a manner which may adversely affect the blood. For example, when an increase in $pO_2$ was desired, it could be effected only by a substantial increase in the flow of oxygen with respect to the flow of blood into the device. A high gas-to-blood-flow ratio represented an inefficient operation of the oxygenator and, more importantly, substantially increased the risk of hemolysis.

The present invention provides features enabling improved blood bubble formation and blood bubble flow which result-in substantially improving the oxygenating capabilities of the oxygenator. In particular, the present invention provides for improved flow of blood bubbles along the passageway within the oxygenating chamber as well as improved blood bubble formation. Such improved flow and bubble formation avoid the situation in which relatively few nonuniform blood bubbles are initially generated and then not adequately mixed with free oxygen to effectuate optimum oxygen-carbon dioxide transfer without harm to the blood.

Furthermore, the present invention provides for an improved structure such that the volume of priming liquid for start-up of the oxygenating device can be substantially reduced. This reduction is advantageous in the commonly occurring situations where either blood (not that of the patient) alone, blood mixed with a solution for hemo-dilution, or hemo-dilution solution alone is used for priming the oxygenator. The reason why such reduction is advantageous in the first situation mentioned above, i.e., when blood (not that of the patient) alone is used as priming liquid, is that the less liquid used which is not the blood of the patient, the more physically acceptable is the oxygenating process to the patient. The reason for the advantage in the second situation, i.e., when blood mixed with a solution for hemodilution is used as priming liquid, is the one just mentioned, as well as the fact that blood alone is more readily oxygenated than is blood mixed with hemo-dilution solution because of reduced hematocrit of the latter. Therefore, the less mixture used for priming, the better the oxygenating during the initial operation stages. The reasons for the advantage in the third situation, i.e., when hemo-dilution solution alone is used as priming liquid, are the same as those mentioned above for the second.

The present invention contemplates a blood oxygenating device whereby (a) oxygen to blood transfer can be effectively and efficiently achieved with an improved gas-to-blood flow rate, (b) improved blood and blood bubble flow characteristics can be obtained, (c) improved blood bubble formation can be achieved, and (d) the volume of priming liquid can be substantially reduced.

The present oxygenating device in its preferred embodiment comprises an oxygenating chamber and a heat exchange chamber. The oxygenating chamber comprises generally a bubble column including a bubbler chamber and a mixing chamber or passageway. The bubbler chamber is provided with oxygen and blood inlet means and a diffusion cone. Venous blood entering the bubbler chamber is bubbled by a plurality of small jetting streams of oxygen emanating from the diffusion cone in a direction counter to, for parallel with, the flow of blood to form blood bubbles. The blood bubbles then pass into the mixing chamber. The mixing chamber is provided with a plurality of secondary flow-producing means which function to promote a secondary flow of blood bubbles passing therethrough. The passageway, together with the diffusion cone, controls the bubble size and promotes efficient oxygenation of the blood bubbles. The blood bubbles which exit the oxygenating chamber are required to pass through a heat exchange chamber and a defoaming means before exiting the oxygenating device.

In one embodiment of the present invention, the defoaming means is positioned around the oxygenating chamber. The blood bubbles exit the oxygenating chamber and pass down the outside of the oxygenating chamber through an open space provided by a defoamer support member disposed between the oxygenating chamber and layers of defoamer material encompassing said chamber. The bubbles then flow into the reservoired debubbled blood which extends around the lower end of the chamber and are substantially converted to liquid (or debubbled) oxygenated blood and free oxygen and carbon dioxide gases which are vented. The liquid blood then passes through the defoamer material which surrounds the reservoired blood. Bubbles which do not dissipate during their travel down the outside of the bubbler chamber dissipate as they pass laterally through the defoamer material. After the blood passes through the defoamer material, it flows into the heat exchange chamber for the transfer of heat to the blood prior to its return to the patient. In an alternative preferred embodiment, the blood bubbles are passed through the heat exchange chamber prior to being passed through the defoaming means. The defoamer is disposed around the outside of the heat exchanger and is similarly provided with defoamer support members which function to support the defoamer material spaced apart from the heat exchange chamber, thereby similarly providing an open space for the passage of blood bubbles. After passing through the defoamer material, the blood is returned to patient.

BRIEF DESCRIPTION OF DRAWINGS

A more thorough disclosure of the objects and advantages of the present invention are presented in the detailed description which follows and from the accompanying drawings of which:

FIG. 2 is a side view of the oxygenating device;

FIG. 3 is a side sectional view of the oxygenating chamber;

FIG. 4 is a perspective view of the oxygenating chamber and the defoamer support member illustrating the flow of blood and blood bubbles from the outlet of the chamber;

FIG. 5 is a view of the oxygenating chamber illustrating the placement of the defoamer support member and splash shield;

Figure 1:
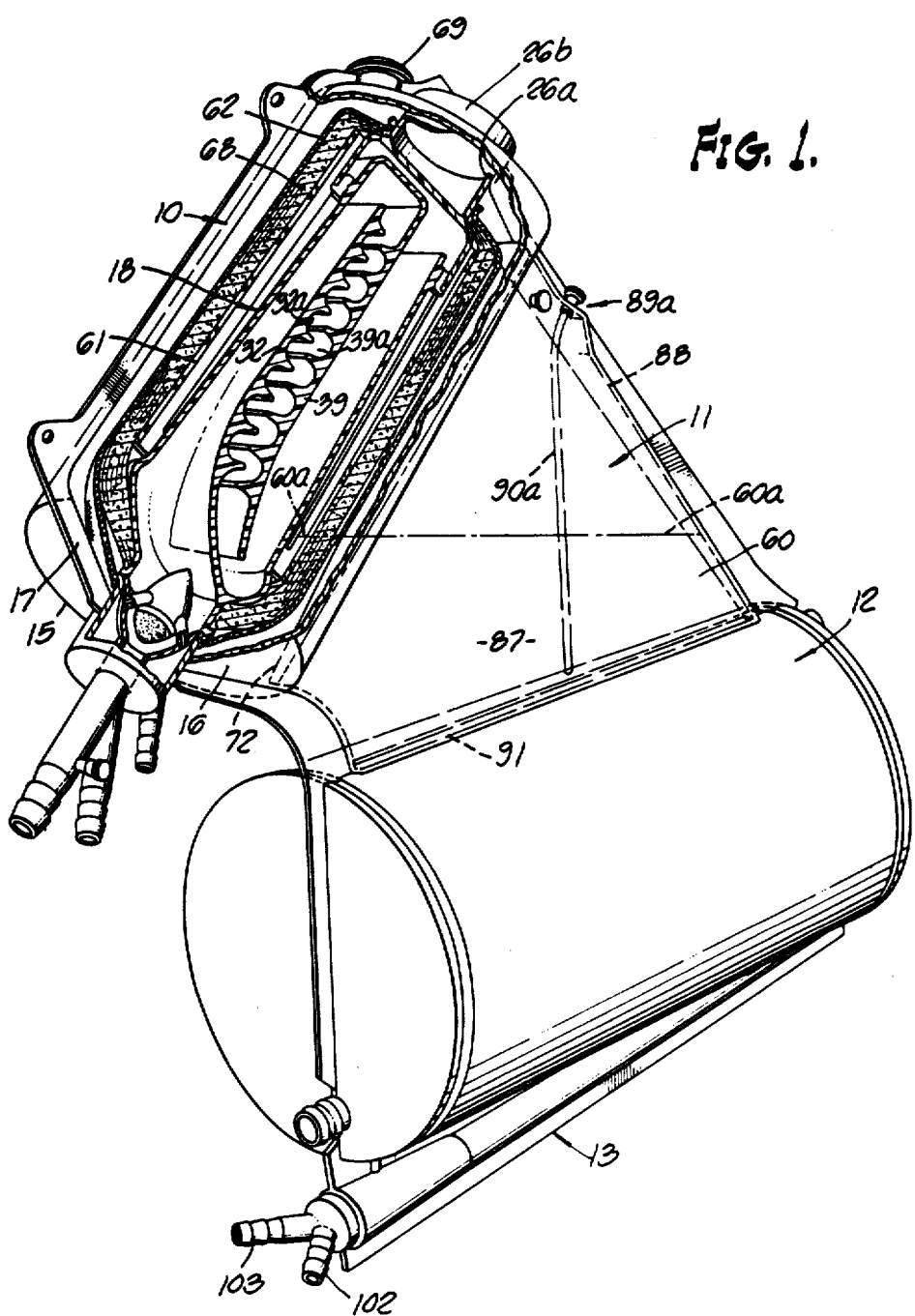
FIG. 1 is a side perspective view of an oxygenating device according to the present invention, partially in section to illustrate the oxygenating chamber and heat exchange chamber.

Referring now in detail to FIGS. 1-6, there is shown one of the preferred embodiments of the oxygenating device according to the present invention. The device comprises an upper cylindrical chamber, generally designated 10 (commonly called an oxygenating chamber), a narrow central chamber, generally designated 11, and a lower cylindrical chamber, generally designated 12 (commonly called a heat exchanging chamber), and a collecting chamber, generally designated 13. In use, the oxygenating device may be suspended by hooks or other appropriate means passing through apertures 14 formed at opposite ends of the upper chamber 10. When in normal operation, the angle formed by the axis of the upper cylindrical chamber 10 with the horizontal is preferably in the range of approximately 35 to 40 degrees and, more specifically, 37 to 38 degrees.

The chambers 10, 11, 12 and 13 are preferably formed from a polycarbonate plastic (sold by General Electric under the trademark "Lexan") which may either be vacuum formed or injection molded to shape two self-sustaining substantially rigid shells 15 and 16 which are substantially identical to each other except one is the mirror image of the other. The two shells are each provided with a coplanar peripheral flange 17, and the peripheral flanges of the two shells are adhered together by a suitable adhesive or other methods of bonding to form a unitary, transparent structure. The plastic is inert, nontoxic, impervious to the passage of gases and liquids, and sterilizable. It contains no leechable plasticizers which may be traumatic to the blood, and it is exceptionally strong and durable in order to withstand accidental blows or shocks.

The upper structure or oxygenating chamber 10 comprises the bubbler assembly generally designated 18 in the instant invention, which bubbler assembly is preferably mounted so that its longitudinal axis substantially coincides with the longitudinal axis of the cylindrical chamber 10. The function generally of the bubbler assembly is to intermix oxygen gas with incoming venous blood so as to form films of blood in bubble form, which blood bubbles are advanced in an oxygen atmosphere through the bubbler assembly to an outlet. The oxygen atmosphere exists within each of the blood bubbles as well as in the chamber surrounding the bubbles and the thin films of venous blood exposed to the oxygen effects a transfer of oxygen gas to the hemoglobin in the blood and the consequent release of carbon dioxide from the hemoglobin of the blood.

In effecting this oxygen-carbon dioxide exchange, it is particularly important that as many bubbles as possible of uniform size be formed, and that there be a thorough intermixing of blood bubbles in the passageway of the bubbler assembly and continuous movement of the blood bubbles throughout the entire passageway to avoid pooling in the passageway. Similarly important is the control of the size of the blood bubbles as they progress through the passageway. The structure of the instant bubbler assembly has proven to be extremely efficient in this regard and has shown a capability of being able to maintain a desired physiological oxygen to carbon dioxide ratio at improved gas-blood flow ratios. The bubbler assembly has further shown a capability of effecting a substantial increase in the oxygenation of blood over the range of both high and low blood flow rates.

The detailed structure of the bubbler assembly 18 is best shown in FIGS. 1 and 3 and all parts of the bubbler assembly are preferably formed from the polycarbonate plastic material referred to previously. Referring to FIG. 3, the bubbler assembly or column 18 includes a hollow, elongated housing, generally designated 19 and comprises generally bubbler or bubbling chamber 53 and a continuous closed mixing passageway 20. A closure plate 21 is disposed at one end of the bubbler assembly and carries venous blood inlet means, generally designated 22, and an oxygen inlet means, generally designated 23. The closure plate 21 has a peripheral flange 24 which is adhered to the lower end of the bubbler assembly housing 19 by suitable adhesive to provide an airtight seal. The other end of the bubbler assembly housing 19 is covered with a cap or cover member, generally designated 25, which is removably mounted on four tabs, generally designated 25a, affixed circularly 90 degrees apart on the outside of the housing 19. The cover member preferably is generally circularly shaped and is provided with an overhanging portion 26, which is spaced outwardly of the sides of the housing 19 by the tabs 25a so as to afford an outlet opening 27 which extends 360 degrees around the housing 19 for blood and blood bubbles, generally designated 28. Such an outlet provides for improved flow through the bubbler assembly. The cap member 25, when positioned on the tabs 25a, is approximately one eighth of an inch from the uppermost portion 28 of the bubbler assembly 18. The housing 19 is partitioned so that a continuous closed mixing passageway 20 is divided into a plurality of passageway segments. An upper segment 30 is defined by a generally rounded upper wall 31 and a generally planar bottom wall 32 which extends from a bubbler chamber 53 at the inlet section 33 upwardly and rearwardly away therefrom to a downwardly returned rounded end portion 34. The interior surface 35 of portion 34 directs fluid from a downstream outlet end 36 of segment 30 into a juncture portion 37 by means of which upper segment 30 is in communication with a vertically adjacent mixing segment 38 where blood bubbles are uniformly mixed with free oxygen. The cross-sectional flow area of the passageway 20 which is relatively large at the inlet section 33 smoothly tapers inwardly or decreases as it extends to the outlet end 36 and through juncture portion 37. Fluid is further directed downwardly and forwardly by the segment 38.

Mixing segment 38 is defined by the undulate wall 32a, which is the reverse side of the generally planar wall 32, and an undulate lower wall 39a. In the preferred embodiments, each of the walls 32a and 39a is comprised of a series of arcuate sections or secondary flow-producing deflecting protrusions 38a in end-to-end relationship to provide a serpentine passageway. As the blood bubbles pass through the serpentine passageway, they are subjected to secondary flow which substantially increases the efficiency of the oxygen-carbon dioxide exchange. The secondary flow is a gently swirling or rotating flow of blood bubbles. Secondary flow is imparted to the stream of blood bubbles as they pass through the rounded portions of the arcuate sections comprising the serpentine passageway. The blood bubbles are, thus, continually swirling and rotating as they flow through the length of the serpentine passageway. This gentle turning or rotating of blood bubbles significantly facilitates oxygenation of the blood. Segment 38 extends from its juncture 37 at the rear in communication with upper segment 30 to a forward outlet end 40 where it joins with a lower segment 41. The cross-sectional flow area of passageway 20 first increases slightly as it extends from its upstream inlet end at the juncture 37 to a midsection 41a and then decreases as it extends toward the outlet 40. The interior surface 42 of rounded end portion 43 directs fluid through a juncture portion 44 by means of which segment 38 communicates with segment 41. Outlet end 40 and, more particularly, juncture portion 44 define a section of the passageway 20 having reduced or restricted cross-sectional flow area which is slightly smaller than the cross-sectional flow area of the passageway 20 at the outlet 36 and juncture portion 37. Fluid is returned rearwardly of segment 41 by the interior surface 42 of rounded rearwardly returned wall portion 43. Lower segment 41 leads away from its juncture at 44 with mixing segment 38 to the outlet means 27 remote from the inlet section 33. Lower passageway segment 41 is defined by the generally planar wall 39, which is the reverse side of the undulate lower wall 39a, and a generally rounded bottom wall 46. The cross-sectional flow area of the passageway 20 in the lower segment 41 increases as it extends from the juncture 44 to provide for a relatively large and unrestricted cross-sectional flow area throughout the length of segment 41.

Thus, blood entering generally through the inlet area will travel an inverted S-shaped path first passing through the upper segment 30, thence being directed downwardly and returned forwardly through the mixing segment 38 and thence being directed onwardly and returned rearwardly through the lower segment 41 from which it is passed outwardly through outlet means 27. In the sections of the passageway 20 where cross-sectional flow area is decreased, the flow is accelerated therein to insure continuous flow throughout the bubbler assembly and, thereby, reduce pooling. Moreover, the variations of the cross-sectional flow area of the passage 20 control the size of the blood bubbles as they flow through the bubbler assembly. That is, the blood bubbles are the smallest when first formed at the bubbling section where the pressure acting on the blood bubbles, as a result of the downstream bubbles above, is greatest. As the blood bubbles progress upwardly in the passage way segment 30, the pressure decreases and the size of the bubbles increases. However, as the cross-sectional flow area of the passageway 20 decreases, the flow therethrough is constricted and the bubble size is again reduced. Thus, the pattern of the bubble size as the bubbles progress through the bubbler assembly is such:

Bubble size is the smallest when the bubbles are first formed in the bubling section 33; bubble size increases as the blood bubbles begin to progress upwardly in the segment 30; bubble size decreases as the blood bubbles move to and through the outlet 36 and juncture 37; bubble size increases as the blood bubbles progress through the segment 38 from the juncture 37 to the midsection 41a of the segment 38 and then decreases as the blood bubbles progress to and through the outlet end 40 and junction 44; and, finally, bubble size increases as the blood bubbles progress from the juncture 44 through the segment 41 to the outlet means 27.

It is believed that due to the fact that the atmosphere within the device comprises more oxygen than carbon dioxide, blood bubbles more readily accept oxygen on the surface of the bubble and more readily dissipate carbon dioxide into the interior of the bubble. Thus, it is believed that the larger bubbles dissipate carbon dioxide more efficiently and the smaller bubbles oxygenate more efficiently. Therefore, this control of the bubble size, and in particular the variations of bubble size as the blood bubbles progress through the passageway 20 is considered to be very important in effecting the desired gas-blood transfer.

At the inlet section 33 is bubbling chamber 53, which includes a cone-shaped wall member 50 that supports a generally egg-shaped diffusion cone 51 by three legs 51a. The legs 51a are hollow and provide a passageway from the exterior of the cone-shaped wall member 50 to the interior of the diffusion cone 51 for oxygen which is introduced into the area between the cone-shaped wall member 50 and the closure plate 21 by way of the oxygen inlet means 23. The legs 51a are formed as part of the top portion 51b of the diffusion cone 51, this top portion being constructed of polycarbonate plastic. Bonded to top portion 51b is the bottom portion 51c of the diffusion cone which is formed of porous polyethylene material available commercially as "Porex" high density polyethylene from the Porex Division of Glasrock Products, Inc. with a plurality of minute apertures 51d through which oxygen is admitted into the housing 19. This material is prepared by sintering particles of polyethylene to produce a porous structure having relatively uniform pore sizes. Other plastic materials such as polypropylene and polyvinylidene fluoride can be processed in the same manner as described in the brochure "Porex Porous Plastics for Industry, Science and Medicine", which is incorporated by reference herein. The pore size may vary, with 10–30 microns being suitable and 20 microns preferred. Alternatively, perforated members, e.g., of the type disclosed in U.S. Pat. Nos. 3,488,158 and 3,578,411 may be used.

Figure 6:
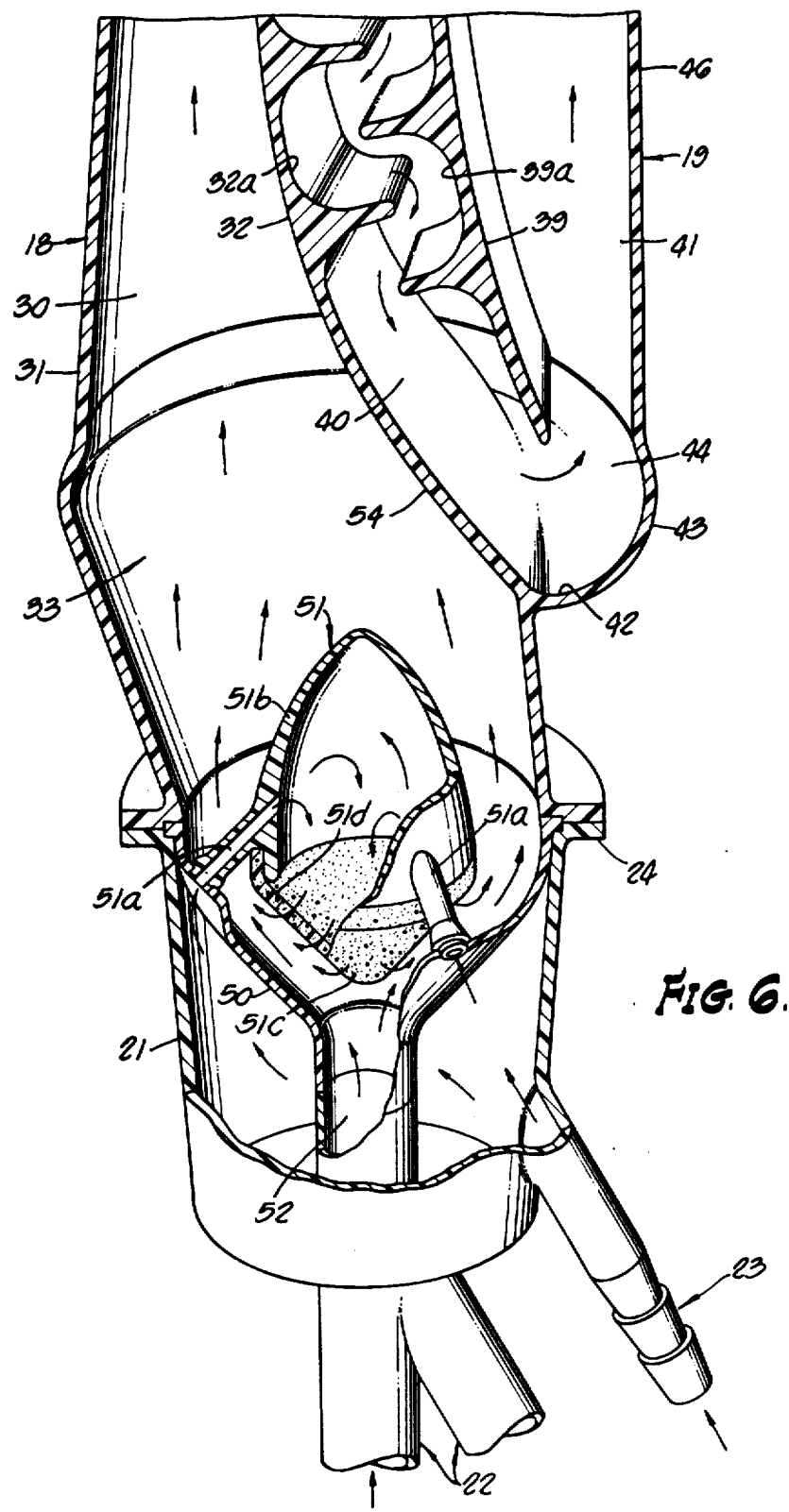
FIG. 6 is a perspective view of the bubbler chamber and the diffusion cone illustrating the flow of blood and oxygen into the bubbler chamber and the formation of blood bubbles.

As can be seen in FIG. 6, the inner diffusion cone is centrally disposed within chamber 53 and the inner surface of the cone-shaped wall member 50 provides a divergent mouth for the inlet port 52 of the blood inlet means 22 and the bottom portion 51c directly opposes the inlet pore 52. As venous blood flows out of the inlet port 52, the laminar flow thereof is disturbed and secondary flow or turbulence is induced. The blood is uniformly distributed around the diffusion cone 51 and immediately bubbled by the multitude of tiny jetting streams of oxygen pointed directly into the flow of blood. By constructing the bottom portion of the diffusion cone out of Porex porous polyethylene, bubbles of small diameter, as well as relatively uniform bubbles, can be formed. The location and structural arrangement of the diffusion cone provides not only for uniform distribution of incoming venous blood so that substantially all of the incoming blood is quickly formed into bubble films with effective rapid exposure of the blood in film form to an oxygen atmosphere, but also for the uniform distribution of bubbled blood flowing into the continuous closed mixing passageway 20. The number of bubbles formed, the uniformity of the bubbles, and the flow distribution of the incoming venous blood, as well as the bubbled blood passing into the closed passageway, all, individually and in combination, significantly contribute to a more efficient oxygenation process.

Although the above described structure is preferred for combining the incoming blood and oxygen, a porous or permeable membrane may be used or the porous plastic may be provided with such a membrane on its outer surface to achieve greater uniformity of bubble size.

Still further, the diffusion means may be of virtually any configuration, e.g., conical, tubular, etc., but it is believed that the embodiment shown in the drawings results in a high degree of efficiency with minimum risk of blood damage.

In the embodiments shown, a venturi effect is created as the incoming blood passes around the diffusion cone.

As seen in FIG. 3, the housing 19 is upwardly inclined when in operative working position. The blood bubbles initially formed in the bubbler chamber 53 are guided upwardly by inclined surface 54 into the upper passageway segment 30. Within segment 30 some bubbles may burst and reform droplets of blood, while still other small quantities or droplets of blood may be carried along in the upward progress of the bubbled blood in the segment 30. However, as droplets of blood form, the droplets gradually gather together and flow back downward by gravity into the bubbler chamber 53 once more where the blood is again rebubbled and moved once more up the passageway segment 30.

As the blood bubbles pass through the outlet means 27 of the bubbler assembly 18, the bubbles flow down the outside of housing 19 to liquid blood reservoired in the oxygenating chamber 10. The level of this reservoired blood is identical to that in the blood reservoir 60 of the central chamber 11 and is approximately indicated by the phantom line 60a shown in FIG. 1. Some of the bubbles may dissipate and form droplets of blood as they flow down the outside of housing 19, while other bubbles may dissipate as they contact the liquid debubbled blood reservoired around the outside of the lower end of the oxygenating chamber.

Referring to FIGS. 1 and 5, situated on the outside of the bubbler assembly 18 is a defoamer support means 61 which provides the space between the bubbler assembly 18 and defoaming means 62 for the blood bubbles to freely pass from the outlet means 27 to the reservoired blood. This defoamer support means 61 is preferably constructed of polypropylene in a latticework fashion, having a plurality of spacing segments 63 parallel to each other and a plurality of holding bands 64, which are parallel to each other, but affixed to the spacing segments 63 perpendicular thereto with such holding bands 64 fixedly positioned at each end of the spacing segments 63. Certain of the holding bands 64 are longer than others and have pins 64a affixed to ends thereof, which extend radially out from the longitudinal axis of the chamber 10, and holes 64b in the other ends to accommodate said pins 64a. This arrangement allows for the defoamer support means to be fastened into place when wrapped around the outside of the bubbler assembly 18 by snapping the pins 64a into the holes 64b.

As shown in FIG. 4, the spacing segments 63 are preferably so constructed as to have one side which incorporates a seating extension 65 at one end and a cap indentation 66 at the other end. The other three sides of the spacing segments 63 are flat and the holding bands 64 lie across the flat side of each spacing segment 63 opposite the seating extensions 65 and the cap indentations 66.

As shown in FIG. 5, the defoamer means 61 is wrapped around the bubbler assembly 18 with the spacing segments 63 running parallel to its longitudinal axis and with the holding bands 65 circumscribing the bubbler assembly 18 perpendicular to its longitudinal axis. The only portions of the defoamer support means 61 that contact the bubbler assembly housing 19 are the seating extensions 65, which do so at the lower end of the bubbler assembly housing 19 at a bulging portion 67 thereof, which provides a restricting surface upon which the seating extensions 65 rest, holding the defoamer support means 61 in its desired position relative to the bubbler assembly 18. The cap indentations 66 at the upper end of the defoamer support means 61 provide an opening whereby the cap member 25, which covers the top of the bubbler assembly 18, can be placed in its operating position between the defoamer support means 61 which extends to approximately the top wall 25b of the cap member 25 when the oxygenating chamber 10 is in its fully assembled configuration.

The defoamer support means 61 is held in position around the bubbler assembly 18 by the defoaming means 62, which it supports away from the bubbler assembly housing 19 approximately one-half inch. The defoaming means 62 is preferably formed in the shape of a sleeve which is open at both ends, fits over the outer lateral surface of the defoamer support means 61 and has a drawstring at its lower open end which is drawn tightly around the bubbler assembly 18 so that all the blood flowing out of the bubbler assembly 18 will be caused to flow through the defoaming means 62. The upper portion of the bag, when fitted over the defoamer support means 61, fits snugly around a cylindrical segment 26a of the cap member 25 which connects with the top wall 25b of the cap member 25 and extends out therefrom. This arrangement affords a window so that an operator of the oxygenating device can see that blood bubbles are being formed properly. The sleeve is constructed of a plurality of similarly shaped sleeve layers 68 of knitted mesh material, which layers are nested one within another to provide a multitude of tortuous paths of flow. The knitted layers 68 are preferably formed of polypropylene fibers (polyurethane foam also being acceptable) each of which is generally smooth and round and presents no rough surfaces (which may cause damage to the red cells) to the flow of blood passing therethrough. The polypropylene layers 68 are impregnated or coated with a nontoxic antifoam composition of the medical silicone antifoam type which is well known in the art.

Thus, as blood bubbles collect on the surface of the reservoired blood and move outwardly on the surface, they contact the defoaming layers, reducing the surface tension of the bubbles which dissipates them, and rivulets of oxygenated blood are formed, freeing excess oxygen and carbon dioxide which escape the bubbler assembly via outlet means 27, then pass through the defoaming means 62 and a porous bag 70 which surrounds the defoaming means, and finally exit the oxygenating chamber 10 through port 69 (shown in FIG. 1) provided for such purpose near the top of the oxygenating chamber. The same is true for any blood bubbles that might contact the defoaming means 62 before reaching the blood reservoired in the oxygenating chamber within the defoaming means.

As shown in FIG. 5, a porous bag 70 covers the defoaming means 62 in the same way that the defoaming means covers the defoamer support means 61, but has drawstrings at both its open ends, which are drawn tightly around the bubbler assembly 18 and cap member 25 so that all the blood and gas flowing out of the bubbler assembly 18 will be caused to pass through the bag 70. This bag 70 aids in holding the defoaming means 62 in its shown configuration. Also, the bag 70, preferably formed of nylon material and having a pore size of about 150 microns, filters blood as it exits the bubbler assembly 18. In the adult size oxygenator, the bag 70 preferably has a surface area of approximately 144 sq. in. Also, in the adult size oxygenator, it is preferred to provide about 4 or 5 layers 68 of the polypropylene mesh, while in the pediatric and infant size the number of layers may be decreased.

Between the defoaming means 62 and the porous bag 70, a polyethylene sheet 71 is positioned so as to extend about the bottom of the bubbler assembly 18 for nearly 120 degrees. The arcuately disposed lower marginal edge of the polyethylene sheet 71 is normally positioned about four inches upwardly of the lower end of the oxygenating chamber 10, and the upper arcuate marginal edge of the sheet 71 extends beyond the cap member top wall 25b. This sheet 71 is fastened to the defoaming means 62 by tack-like buttoners 71a which have barbed ends that pass through the sheet 71 and extend into the defoaming means 62. The polyethylene sheet 71 constitutes a troughlike formation for directing the flow of any debubbled blood passing through the defoaming means 62 before reaching the reservoired blood in the oxygenating chamber 10. This sheet 71 causes such debubbled blood to flow angularly downwardly through the defoaming means 62 within the sheet 71, helping to maximize the debubbling operation, and causes the blood to gradually flow to the lower end of the oxygenating chamber 10 so as to make a smoother exit therefrom through exit opening 72 (shown best in FIG. 1). Normally, debubbled blood is collected just past opening 72 and if sheet 71 were not present, some of the debubbled blood from the oxygenating chamber 10 might drip down and splash on such collected blood, causing undesirable bubbling.

As best seen in FIG. 1, the bubbler assembly is centered with respect to the oxygenating chamber and held away from the interior surfaces thereof by the cylindrical segment 26a of the cap member 25 fitting within a cylindrical indentation 26b of the upper wall of the oxygenating chamber 10. This configuration enhances the stability of the bubbler assembly arrangement over previous arrangements in which the bubbler assembly was cantilevered by its lower end and substantially reduces the possibility of the bubbler assembly leaking due to being jarred in handling or floating during the operation.

The narrow central or intermediate chamber 11 provides the reservoir 60 for the oxygenated blood. This central chamber has sidewall portions 87 (only one of which is shown) which are generally rather closely spaced and taper towards each other as they extend both from the oxygenating chamber 10 to the heat exchanging chamber 12 and from the top end of the oxygenating chamber to the bottom end thereof. The sidewall portions 87 round together from the lower end of the oxygenating chamber 10 to the heat exchanging chamber 12 and do the same thing from the upper end of the oxygenating chamber to the heat exchanger. However, due to the greater distance between the sidewall portions 87 essentially the entire way from the upper and of the oxygenating chamber to the heat exchanger, their rounding together forms a "V"-shaped back wall 88 to the central chamber 11 with the flange 17 running down its center.

In use, the lower end of the central chamber or reservoir 11 accommodates a small volume of oxygenated blood relative to the upper end and will fill rather rapidly so that the level of the blood will preferably extend into the lower end of the upper oxygenating chamber 10. This double-tapering structure allows for less priming liquid to be used in the start-up of the oxygenator than is required with the units described in the patents and pending applications listed earlier. This reduction in the needed volume of priming liquid makes the oxygenation process more physically acceptable to the patient when liquids other than his own blood are used for priming, since the less liquid (not the blood of the patient) used, the more acceptable the process to the patient, and helps afford better oxygenation when mixtures of blood and solutions for hemo-dilution are used, since blood alone is more readily oxygenated than blood mixtures and the smaller volume of such mixtures used, the better the oxygenation.

This double-tapering structure also provides for uniform blood flow through the central chamber 11, which substantially reduces the possibility of platelets collecting on the sidewall portions 87. The reason this structure provides for uniform flow stems from the fact that in its operating position the oxygenator is in an inclined position as discussed earlier and due to this inclination, blood tends to flow through the central chamber 11 more rapidly at the front, i.e., the portion nearest the inlet means 22, thereof when the cross-sectional flow area across a horizontal plane of the central chamber is uniform from front to back. By incorporating the structure just described, the cross-sectional flow area across a horizontal plane decreases in the central chamber proceeding from front to back which neutralizes the tendency for greater flow rates to exist nearer the front of the chamber and allows for the uniform flow that is advantageous from the standpoint of reducing the collection of platelets on the sidewall portions 87 of the central chamber 11.

In operation, blood enters the oxygenating chamber 10 through blood inlets 22 and oxygen is fed into the oxygenating chamber through inlet 23. The blood and oxygen are intermixed and travel through the passageway in the interior of the bubbler assembly 18 and mixed, particularly, through upper segment 38 and, finally, through the outlet means 27 defined by the cap member 25. After passing through this outlet, the blood passes outwardly and downwardly of the exterior of the bubbler housing 19 to the reservoired blood and through the defoaming means 62 and then into the central chamber 11.

In central chamber 11, the blood is held in a vertical generally sheet-like column and flows therefrom by means of opening 91 into the heat exchanging chamber 12 so that its temperature can be raised before return to the patient. From the heat exchanging chamber, the blood travels to the bloodcollecting chamber 13 from which it may be returned to a patient through discharge ports.

Figure 7:
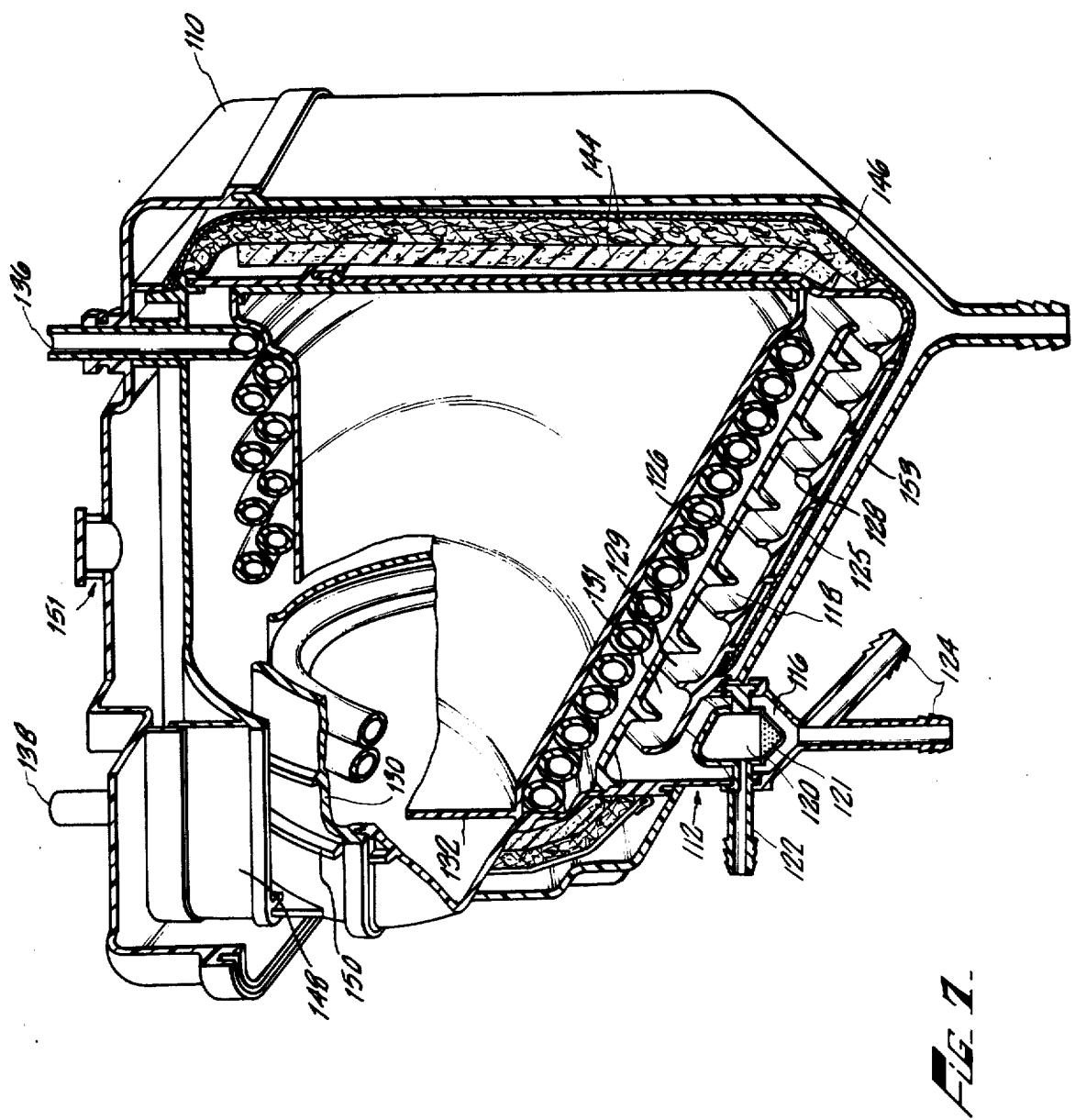
FIG. 7 is a perspective view, partially in section, of an alternate embodiment of the oxygenating device illustrating the oxygenating chamber and the heat exchange chamber.
Figure 8:
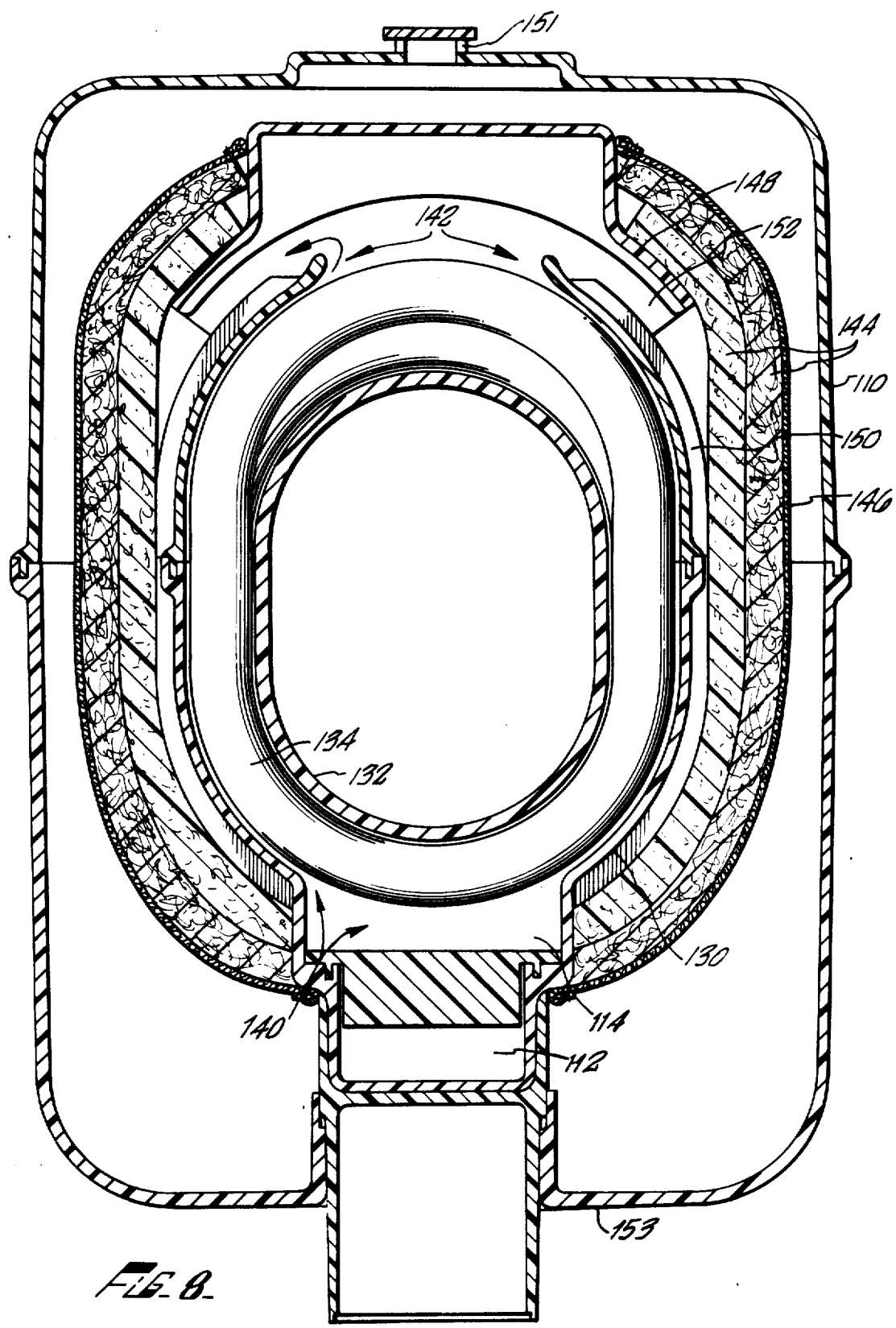
FIG. 8 is a cross-sectional view taken along line 8—8 of FIG. 7.

Referring to FIGS. 7 and 8, there is shown an alternate preferred embodiment of the blood oxygenator of the present invention. The oxygenator is generally comprised of outer housing 110 having disposed therein an oxygenating chamber 112 and a heat exchange chamber 114. The various parts of the oxygenator are also preferably comprised of polycarbonate material. The oxygenating chamber comprises generally bubbler chamber 116 and mixing passageway 118. The bubbler chamber is provided with a similarly formed diffusion cone 120 which is supported by oxygen inlet 122. The bottom portion 121 of the diffusion cone is preferably similarly comprised of a porous polyethylene having pore sizes from approximately 10 to 30 microns. The bubbler chamber is additionally provided with venous blood inlets 124 which open into the bubbler chamber 116. The diffusion cone is preferably similarly centrally disposed within the chamber 116 to disturb the laminar flow of entering blood. The diffusion cone so situated similarly enables the introduction of a substantial portion of oxygen into the bubbler chamber in a direction directly counter to the incoming flow of blood.

The mixing passageway 118 is similarly provided with upper and lower undulate walls 125 and 126 respectively, preferably extending along the entire length of the mixing chamber 118. The undulate walls 125 and 126 similarly comprise a series of arcuate secondary flow-producing deflecting sections or protrusions 128 which are positioned to form a serpentine passageway. The serpentine passageway similarly functions to cause secondary flow of blood bubbles as they pass therethrough. The cross-sectional flow area of the mixing passageway is similarly varied along its length to control the size of the blood bubbles. The arcuate protrusions 128 are offset so that the distance 129 between opposing arcuate protrusions is less than the distance 131 between successive opposing arcuate protrusions. The cross-sectional flow area is therefore successively increased and decreased along the entire length of passageway 118. This variation in cross-sectional flow area improves the oxygenating capabilities of the oxygenator.

The heat exchange chamber 114 is disposed within an inner housing 130 and is comprised of a generally frustrum-shaped enclosure 132 having a heating conduit 134 helically wound around the enclosure. The heating conduit is preferably formed from a thermally conductive metal having a biocompatible coating. The heating conduit is provided with inlet means 135 and outlet means 138. The wall of the inner housing-130 and the wall of the enclosure 132 define a narrow passageway 140 which contains the heating conduit and enables the blood exiting the ,mixing chamber 118 to flow up through the inner housing in close contact with the heating conduit. The thin film of the blood bubbles enables more efficient heat transfer from the heating conduits to the blood, thereby enabling more efficient regulation of the tmperature of the blood. The top of the inner housing 130 is provided with a longitudinal slot 142 to enable the blood bubbles to exit the inner housing.

The defoaming means 144 is disposed around the outside of inner housing 130. The defoaming means is preferably similarly comprised of knitted polypropylene or, alternatively, polyurethane foam or combinations of foams and the defoaming means is preferably impregnated with a silicone antifoam composition. The defoaming means 144 is further provided with a similar porous bag 146 which is disposed around the outside of defoaming means and functions to support the defoaming means against inner housing 130. The bag 146 is provided with a drawstring which is secured to the outside of the oxygenating chamber 112 and to the downstanding flange 148 which is connected to outer housing 110. The defoaming means 144 is positioned around the outside of the inner housing 130 in such a manner that the blood bubbles passing out from slot 142 must pass through the defoaming means before exiting housing 110, but the liquid blood simply flows down the outer surface of housing 130. The wall of inner housing 130 is preferably provided with a plurality of defoamer support ribs 150 which function to support the defoamer means 144 spaced apart from the wall of the inner housing, thereby similarly providing an open space 152 for the passage of blood bubbles exiting slot 142. The defoamer is also similarly provided with a polyethylene sheet disposed between the defoamer and the porous bag. The sheet functions as a trough to direct the flow of any debubbled blood within the defoamer.

In operation, the venous blood enters the housing through inlet 124 and oxygen enters the housing through oxygen inlet 122. The blood flows into bubbler chamber 116 and is immediately converted into blood bubbles as it passes by diffusion cone 120. The blood bubbles flow out of the bubbler chamber and up into mixing passageway 118. Upon exiting the mixing passageway 118, the blood bubbles flow up into the chamber formed by inner housing 130 through passageway 140 around the heating conduit 134. The blood bubbles exit passageway 140 through slot 142 formed in inner housing 130 and flow into open space 152 formed between the inner housing and defoaming means. The bubbles are dissipated by contact with the reservoired blood in space 152 or are forced into contact with the defoaming means, converting the bubbles into liquid blood and free oxygen and carbon dioxide gases. The free gases exit the housing through port 151 formed in the top of outer housing 110. The debubbled blood flows down the lower wall 153 of the outer housing and exits the housing through outlet 154.

As a result of this invention, blood oxygenators can effectively and efficiently transfer oxygen to blood at an improved gas-to-blood ratio while maintaining a desired physiological oxygen-to-carbon dioxide ratio. In addition, this invention provides for enhanced bubbling and flow characteristics, which provides for more efficient oxygen-carbon dioxide transfer and an overall more efficient oxygenating process, thereby permitting a lower gas to-blood flow ratio which results in lower hemolysis levels. Further, this invention results in an oxygenator which allows for a reduction in the volume of priming liquid required for a start-up and operation of the unit.

While embodiments and applications of this invention have been shown and described, it will be apparent to those skilled in the art that many more modifications are possible without departing from the inventive concepts herein described. The invention, therefore, is not to be restricted except as is necessary by the prior art and by the spirit of the appended claims.

I claim:

1. A method of oxygenating blood which method comprises forming bubbles in blood with an oxygen-rich gas in a bubble-type blood oxygenator which oxygenator contains a bubble column, a portion of said column having a serpentine passageway formed therein to promote secondary flow of blood bubbles passing therethrough, said serpentine passageway comprising a pair of undulate walls, each wall having a continuous series of projecting sections oriented into the serpentine passageway, said sections on said undulate walls forming a plurality of opposing sets of protrusions, said protrusions from said opposing sets being offset from each other to form a substantially unrestricted passageway therethrough.

2. The method of claim 1 wherein said blood containing said bubbles is subjected to heat transfer.

3. A method of oxygenating blood which method comprises forming bubbles in blood with an oxygen-rich gas in a bubble-type blood oxygenator having therein a bubble column having a first end and a second end, said bubble column being provided with at least one segment having a serpentine passageway formed therein to promote secondary flow of blood bubbles passing therethrough, said serpentine passageway comprising a pair of undulate walls, each wall continuous series of arcuate sections, said sections on said undulate walls forming a plurality of opposing sets of spaced-apart protrusions extending into the serpentine passageway, each protrusion from said opposing sets being offset from each other to form a substantially unrestricted passageway therethrough.

4. The method of 3 wherein said blood containing said bubbles is subjected to heat transfer.

5. A method of oxygenating blood which method comprises forming bubbles in blood with an oxygen-rich gas in a bubble-type oxygenator having therein a bubble column having a first end and a second end, said bubble column being provided with a plurality of segments in end-to-end relationship, at least one of said segments having a serpentine passageway formed therein to promote secondary flow of blood bubbles passing therethrough, said passageway comprising a pair of undulate walls, each wall having a continuous series of arcuate sections with a plurality of turns so that said blood bubbles are continuously rotated throughout their passage through said passageway.

6. The method of claim 5 wherein said blood containing said bubbles is subjected to heat transfer.

7. The method of claims 1,3, or 5 wherein said oxygenator has a blood inlet and a blood outlet, a defoaming means positioned between said blood inlet and said blood outlet and wherein said serpentine passageway is positioned between said blood inlet and said defoaming means.

8. The method of claims 2, 4 or 6 wherein said oxygenator has a blood inlet and a blood outlet, a defoaming means positioned between said blood inlet and said blood outlet and wherein said serpentine passageway is positioned between said blood inlet and said defoaming means.

* * * * *

UNITED STATES PATENT OFFICE
CERTIFICATE OF CORRECTION

Patent No. 4,623,518             Dated November 18, 1986

Inventor(s)     Raible, Donald A.

It is certified that error appears in the above-identified patent and that said Letters Patent are hereby corrected as shown below:

In column 14, line 6, after "each wall" insert---having a-----

Signed and Sealed this

Twenty-eighth Day of June, 1988

Attest:

DONALD J. QUIGG

Attesting Officer      Commissioner of Patents and Trademarks